United States Patent [19]

Mollenauer et al.

[11] Patent Number: 5,106,054
[45] Date of Patent: Apr. 21, 1992

[54] SELF-SEALING HEMOSTASIS VALVE APPARATUS AND METHOD OF FORMING THE SAME

[75] Inventors: Kenneth H. Mollenauer, Santa Clara; Thomas A. Howell, Palo Alto, both of Calif.

[73] Assignee: Thomas J. Fogarty, Portolo Valley, Calif.

[21] Appl. No.: 572,618

[22] Filed: Aug. 23, 1990

[51] Int. Cl.$^5$ .............................................. F16L 37/28
[52] U.S. Cl. ................................. 251/149.1; 604/167; 604/256; 604/905
[58] Field of Search ..................... 604/256, 167, 905; 251/149.1

[56] References Cited

U.S. PATENT DOCUMENTS

| | | | |
|---|---|---|---|
| 729,423 | 5/1903 | Scheiber et al. | |
| 2,797,837 | 7/1957 | Roberts | 215/74 |
| 3,086,797 | 4/1963 | Webb | 285/242 |
| 3,197,173 | 7/1965 | Taubenheim | 251/6 |
| 3,438,607 | 4/1969 | Williams et al. | 251/9 |
| 3,920,215 | 11/1975 | Knauf | 251/7 |
| 3,970,089 | 7/1976 | Salce | 128/348 |
| 3,977,400 | 8/1976 | Moorehead | 128/214.4 |
| 4,243,034 | 1/1981 | Brandt | 128/214.4 |
| 4,484,916 | 11/1984 | McPhee | 604/256 |
| 4,580,573 | 4/1986 | Quinn | 128/657 |
| 4,634,421 | 1/1987 | Hegemann | 604/34 |
| 4,649,904 | 3/1987 | Krauter et al. | 604/167 |
| 4,857,062 | 8/1989 | Russell | 251/149.1 |
| 4,909,798 | 3/1990 | Fleischhacker et al. | 251/149.1 |
| 4,960,412 | 10/1990 | Fink | 604/256 |

FOREIGN PATENT DOCUMENTS 1023320  3/1953  France .

*Primary Examiner*—A. Michael Chambers
*Attorney, Agent, or Firm*—Limbach & Limbach

[57] ABSTRACT

A self-sealing valve to accommodate the passage of elongate elements. The valve comprises an elastomeric body having a passage extending therethrough which is held in compression by an elastomeric sleeve disposed around the body. The passage includes an enlarged chamber intermediate its ends and at least a portion of the passage takes the form of a puncture. In use, the passage functions to seal around an elongate element extended therethrough and the chamber reduces friction on the element and provides a void into which the material of the elastomeric body may be displaced without disturbing the seal. A method of forming the valve with a bulbous-ended mandrel is also disclosed.

10 Claims, 1 Drawing Sheet

SELF-SEALING HEMOSTASIS VALVE APPARATUS AND METHOD OF FORMING THE SAME

BACKGROUND OF THE INVENTION

The present invention relates to an improved device for forming a seal around shafts or tubes and, in particular, is concerned with a hemostasis valve for sealing around elongate objects of varying sizes. The invention is especially concerned with a seal which will permit an elongate object to be freely passed therethrough and, upon removal of the object, assumes a closed condition.

Historically, shaft seals have been selected from relatively incompressible materials. The theory has been that a seal must fill the gap between two objects, thus permitting no gas or fluid to find or generate a path. It was thought that if the seal material were to compress, such a path would form. Accordingly, seals designed for retaining pressure were deliberately manufactured of highly incompressible material. The resultant seals had little or no compliance or conformance to accommodate variations in the size or shape of the object about which a seal was required. O-rings, for example, accommodate one external and one internal diameter, with slight allowances for manufacturing tolerances of the shaft gland. If deviations from the tolerances are encountered, or if the shaft or gland is out of round, the O-ring is likely to fail or leak unless a deforming compressive force is applied to the O-ring to cause it to come into closer contact with the shaft gland wall.

The latter approach creates significant problems, not the least of which is the limit on the range of deformation. The biggest drawback is the compressive force which the seal transmits to the traversing shaft, especially if the shaft is of a fragile nature. This approach also fails to work if the traversing shaft is not relatively round.

Other types of seals used in the medical field are the "septum" and the "duck-bill". While satisfactory for certain limited purposes, these seals do not provide the advantages of the present invention.

In the septum seal, a septum or diaphragm is used as the sealing element. In order to traverse the seal, a preformed puncture is provided, or a needle is used to generate a puncture within the septum and the transversing shaft is introduced into this puncture. Puncturing of the septum is an added step that is often disliked in busy clinical settings. Finding the puncture hole is also difficult, particularly where lighting is sparse.

The duck-bill seal is commonly used only as a one way valve. It consists of a circular passage that flattens towards the tip, forming an area where two surfaces coact to seal flow from outside the valve. The seal is effective around a shaft only so long as the pressure causing closure of the seal is sufficiently large.

The prior art also suggests deflectable tubular elements which are manually compressed to effect a seal. While effective, this type of seal requires manual actuation and, when in the sealing condition, necessarily creates significant friction between the seal and the object against which the seal is being created. If the object takes the form of an elongate element which is moved relative to the sealing mechanism during placement, the mechanism generally needs to be loosened.

SUMMARY OF THE INVENTION

The apparatus of the invention comprises an elastomeric body having a bulbous chamber formed therein with aligned passages extending between the chamber and opposite sides of the body, at least one of which passages takes the form of a puncture. In the preferred embodiment, the apparatus includes elastomeric compression imparting means received around the elastomeric body to resist expansion of the passages. The elastomeric body may also be formed with a recess in one side thereof which provides a funnel shaped guide for introducing elements into one of the passages.

The invention provides a method of sealing an elongate element for extension through the interior of an elastomeric tube by providing an elastomeric plug which is sealingly received within the tube and formed with a passage extending longitudinally of the tube. The passage includes a chamber formed in the elastomeric plug and aligned sections extending from the chamber through opposite sides of the plug, at least one of which sections takes the form of a puncture.

In the method of manufacturing a self-sealing hemostasis valve according to the invention, an elastomeric body is molded around a mandrel having a bulbous end with a thin shaft extending from one side thereof. The mandrel is withdrawn from the elastomeric body to leave a chamber within the body and a thin passage extending from the chamber through one side of the body. The side of the body opposite said one side is pierced to form a puncture communicating with the chamber.

A principal object of the invention is to provide a hemostasis valve for the passage of an elongate element, which valve functions to seal against the element without the manual application of clamping force and closes upon removal of the element.

Another object of the invention is to provide such a valve which permits the elongate element to slide through the valve with a minimum of frictional resistance.

Still another object of the invention is to provide such a valve which will accommodate elongate elements of varying diameters.

Yet another and more specific object of the invention is to provide such a valve which includes an elastomeric sealing member and means to accommodate expansion of the member, without disturbing the seal to the elongate element.

A further object of the invention is to provide a method for sealing a tube for the extension of an elongate element therethrough, without the necessity of manually clamping against the elongate element.

Another object related to the latter object is to provide such a method which accommodates elongate elements of varying diameters.

Yet another object is to provide such a hemostasis valve and sealing method wherein means is provided to facilitate the guidance of elongate elements through the valve.

Still another object of the invention is to provide a method of manufacturing a hemostasis valve adapted for the passage of elongate elements wherein the valve comprises a single elastomeric body requiring no manual clamping to effect sealing.

Yet another object related to the latter object is to provide such a method wherein the elastomeric body is formed around a mandrel to provide a bulbous chamber within the body with a thin passage extending from the chamber through one side of he body.

Still another object of the invention related to the latter object is to provide such a method wherein a thin passage in the form of a puncture is formed through the body on the side thereof opposite that through which the thin passage is formed by the mandrel.

These and other objects will become more apparent when viewed in light of the following detailed description and the accompany drawings.

DESCRIPTION OF THE PREFERRED EMBODIMENT

Figure 1:
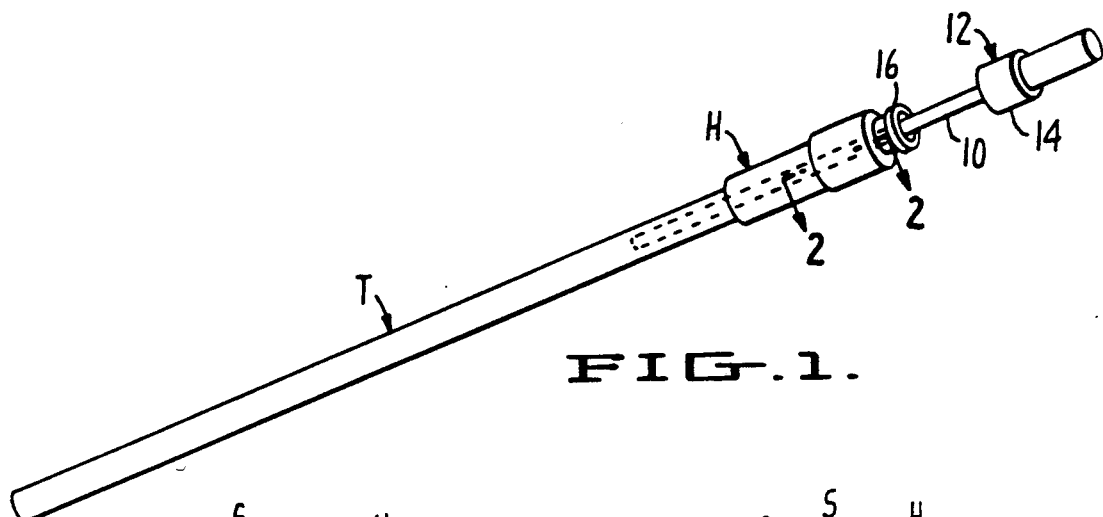
FIG. 1 is a perspective view of a tubular element having a seal incorporated therein constructed according to the present invention, with an elongate catheter extended slidably through the seal.

The valve of the present invention comprises a seal, designated in its entirety by the letter "S", and is shown in FIG. 1 as being incorporated into the elastomeric hub "H" of a tubular sheath "T". A catheter 10 is shown extending through the seal "S". The catheter carries a handle 12 having an internally threaded nut portion 14 threadably engagable with a lug 16 carried by the hub "H". The nut portion 14 and the lug 16 do not form part of the hemostasis valve of the present invention.

Figure 5:
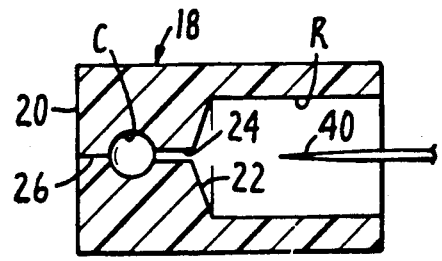

The total construction of the seal "S" may be seen from FIG. 5. There it will be seen that the seal comprises a body comprised of a block of elastomeric material "B" having a cylindrical peripheral surface and a longitudinal axis "A". One end of the block "B" provides a flat side 20. The other end of the block provides a concave conical side 22 at the end of a cylindrical recess "R" formed in the body 18. The conical side 22 is concentric with the axis A. A chamber "C" of a bulbous spherical configuration is formed in the block "B" in generally concentric relationship to the axis "A" and spaced relationship to the sides 20 and 22. A first narrow cylindrical passage 24 extends along the axis "A" from the chamber 24 to the side 22. A second passage 26 in the form of a puncture extends along the axis "A" from the chamber "C" to the side 20. Together, the recess "R", chamber "C" and passages 24 and 26 provide a composite passage extending along the longitudinal axis "A" and fully through the body 18.

Figure 4:
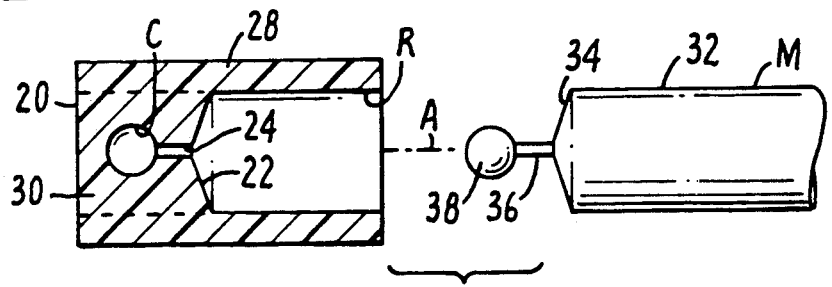
FIG. 4 is a cross-sectional side elevational view of the valve and the mandrel used to form the valve, with the mandrel withdrawn; and, FIG. 5 is a cross-sectional elevational view of the valve, illustrating the stylet used to pierce the valve, with the stylet removed.

FIG. 4 shows the method of forming the elastomeric body 18. As there shown, an elastomeric sleeve 28 has had a mandrel "M" inserted in one end thereof and a volume of elastomeric material 30 has been injected into the other end of the sleeve and around the mandrel to form the chamber "C", the concave conical side 22 and the passage 24. In the preferred embodiment, the sleeve 28 is made of silastic silicone tubing and the volume of material 30 is a silicone adhesive which, when cured, becomes an integral part of the sleeve 28 to form the block "B".

The mandrel "M" corresponds in configuration to the recess "R", side 22, passage 24 and chamber "C" and comprises: an elongate cylindrical section 32 having an outside diameter corresponding to the internal diameter of the sleeve 28; a conical end 34 on the cylindrical section 32; a thin cylindrical section 36 extending concentrically from the conical end 34; and, a spherical ball 38 fixed to the end of the cylindrical section 36 in concentric relationship thereto. As shown in FIG. 4, the mandrel "M" has been used to form the elastomeric material 30 and, after curing of the material, pulled therefrom.

FIG. 5 shows the final step of piercing the passage 26 through means of a stylet 40. As shown in this figure, the stylet has been removed after having been extended through the passage 24 and chamber "C" to form the passage 26.

Figure 2:
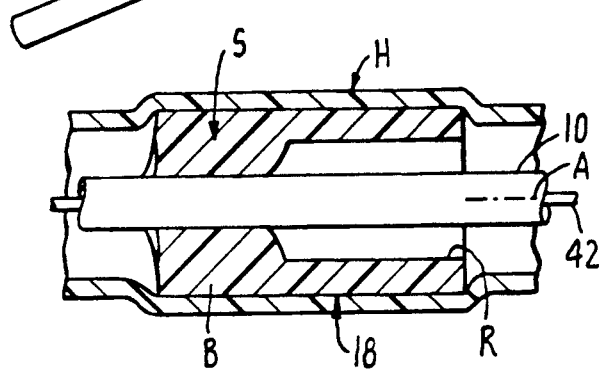
FIG. 2 is a cross-sectional view taken on the plane designated by line 2—2 of FIG. 1.
Figure 3:
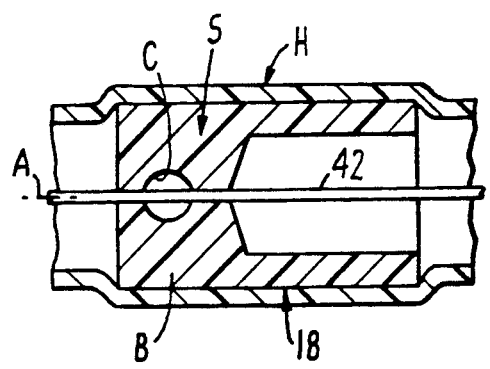
FIG. 3 is a cross-sectional view similar to FIG. 2, illustrating the valve with a thin stylet extended therethrough in place of the catheter.

FIGS. 2 and 3 show the seal "S" received within the elastomeric hub "H". As there seen, the seal forms a plug within the hub. The seal has an outside diameter greater than that of the hub and, thus, the material of the hub is deflected outwardly and imparts compressive force to the seal while accommodating expansion of the passages 24 and 26 and imparting residual sealing stress thereto. Thus, in the assembled condition shown in FIGS. 2 and 3, the volume of elastomeric material 30 is subjected to compressive forces both by the elastomeric sleeve 28 and the material of the elastomeric hub "H".

FIG. 2 shows the catheter 10 sealingly extended through the seal "S". In this example, the catheter has a diameter slightly greater than that of the chamber "C". As a result of this dimensional interrelationship, the catheter 10 displaces the material 30 to the extent that the chamber "C" no longer appears. The chamber "C" advantageously functions to permit such displacement, without interrupting the seal or creating excessive friction between the elastomeric body 18 and the catheter 10.

From FIG. 2, it will also be seen that a thin stylet 42 extends through the catheter 10. FIG. 3 shows the stylet 42 extending slidably through the seal "S", after the catheter 10 has been removed. As shown in FIG. 3, the elastomeric block "B" is in sealing engagement with the periphery of the stylet 42 and that the chamber "C" has reappeared. The punctured construction of the passage 26 assures that a fluid tight seal is provided, notwithstanding the small diameter of the stylet 42, and is maintained even after the stylet is removed. If the stylet has a diameter in excess of that of the passage 24, a seal will also be established between the passage 24 and the stylet.

The length of the passage 26 should be chosen so that the body 18 does not excessively bulge or bind when an elongate object is passed therethrough. An ideal ratio of this length to the diameter of the chamber "C" has been found to be 1:2 to 1:3.

In one exemplary embodiment of the invention, the elastomeric sleeve is made of Dow Corning silastic tubing sold under part number 601-325. This tubing has an OD of 0.192 inches and an ID of 0.110 inches. In this embodiment, the body of elastomeric material 30 was made of Dow Corning RTV-734. The physical dimensions of the resulting seal "S" were as follows:

| | |
|---|---|
| OD of Seal Body | 0.192 inches |

| | |
|---|---|
| OD of Chamber "C" | 0.045 inches |
| OD of Passage 24 | 0.015 inches |
| Length of Passage 24 | 0.0500 inches |
| ID of Recess "R" | 0.110 inches |
| Length of Puncture Passage 26 | 0.015 inches |
| Cone Angle of the Conical End 34 | 30 degrees |

In this embodiment, the stylet used to form the puncture passage 26 had an OD of 0.010 inches. The resulting seal accommodates a shaft of up to 0.092 inches.

Conclusion

While an example and preferred embodiment of the invention has been illustrated and described, it should be understood that the invention is not so limited. For example, the elastomeric material may be something other than silicon, such as latex. The dimensions may obviously vary, depending upon the size of the elongate element to be accommodated. It is the unique construction, rather than the specifics of its material and dimensions, which provides the objects initially set forth herein, and in particular provides for the accommodation of relatively large shafts without excessive drag or tearing of the seal.

We claim:

1. A self-sealing hemostasis valve for the passage of elongate objects, said valve comprising:
    (a) a body comprised of a block of elastomeric material, said body having:
        (1) a chamber formed within and surrounded by said block of elastomeric material;
        (2) aligned passages extending between said chamber and opposite sides of said block, at least one of said passages being in the form of a puncture; and,
    (b) elastomeric compression imparting means received around said body and confining said block to accommodate expansion of the passages and impart residual sealing stress thereto.

2. A valve according to claim 1 wherein the chamber is generally spherical and the passage taking the form of a puncture has a length no greater than one-half the diameter of the chamber.

3. A valve according to claim 1 wherein:
    (a) the body is cylindrical and has a longitudinal axis extending lengthwise of the body;
    (b) the chamber is bulbous and concentric with said longitudinal axis; and,
    (c) the passages extend along said longitudinal axis.

4. A valve according to claim 3 further comprising:
    (a) a recess formed in said body, said recess terminating in a concave conical surface defining one of said opposite sides; and,
    (b) the conical surface is concentric with said longitudinal axis and merges with the passage extending between said one side and the chamber.

5. A self-sealing hemostasis valve for the passage of elongate objects, said valve comprising:
    (a) a body comprised of a block of elastomeric material, said body having:
        (1) a recess therein terminating in a first side of the block disposed within the body;
        (2) a chamber therein in spaced relationship to the said first side and a side of said body opposite said first side, said chamber being disposed within and surrounded by the block of material;
        (3) aligned passages extending between the chamber and said first side and side of the block opposite said first side, at least one of said passages being in the form of a puncture; and,
    (b) elastomeric compression imparting means received around the body and confining said block to accommodate expansion of the passages and impart residual sealing stress thereto.

6. A valve according to claim 5 wherein the chamber is generally spherical nd the passage taking the form of a puncture has a length no greater than one-half the diameter of the chamber.

7. A valve according to claim 1 wherein:
    (a) the body is cylindrical and has a longitudinal axis extending lengthwise of the body;
    (b) the recess is cylindrical and concentric with said longitudinal axis;
    (c) the chamber is bulbous and generally concentric with said longitudinal axis; and,
    (d) the passages extend along said longitudinal axis.

8. A valve according to claim 7 wherein:
    (a) the recess terminates in a concave conical end defining said first side;
    (b) he conical end is concentric with said longitudinal axis and merges with the passage extending between the chamber and said first side.

9. A method of sealing about an elongate element extending slidably through the interior of an elastomeric tube, said method comprising;
    (a) providing a plug comprised of a block of elastomeric material, said plug having:
        (1) a transverse cross-section greater than that of the interior of the tube;
        (2) a chamber formed therein within and surrounded by the block of material;
        (3) aligned passages extending from said chamber through opposite sides of said block, at least one of which passages takes the form of a puncture;
    (b) positioning the plug in within and in compression imparting relationship to the tube with the passages extending generally longitudinally of the tube; and
    (c) extending the elongate element through the passages and chamber.

10. A method of sealing a tube and providing for the extension of elongate elements therethrough; said method comprising:
    (a) providing an elongate pug comprised of a block of elastomeric material, said plug having:
        (1) a longitudinal axis and a peripheral surface generally concentric with said axis;
        (2) a chamber formed therein within and surrounded by the block of material;
        (3) aligned passages extending from said chamber through opposite sides of said block in generally axial alignment with said longitudinal axis, at least one of which passages takes the form of a puncture;
    (b) positioning the plug within the tube with the periphery of the plug in sealed engagement with the tube and the longitudinal axis of the plug extending lengthwise of the tube.

* * * * *

UNITED STATES PATENT AND TRADEMARK OFFICE
CERTIFICATE OF CORRECTION

PATENT NO. : 5,106,054
DATED : April 21, 1992
INVENTOR(S) : MOLLENAUER ET AL.

It is certified that error appears in the above - identified patent and that said Letters Patent is hereby corrected as shown below:

In Col. 6, line 14, change "nd" to --and--.

In Col. 6, line 17, change "claim 1" to --claim 5--.

In Col. 6, line 28, change "he" to --the--.

In Col. 6, line 51, change "pug" to --plug--.

Signed and Sealed this

Seventh Day of September, 1993

Attest:

BRUCE LEHMAN

*Attesting Officer*  *Commissioner of Patents and Trademarks*